United States Patent
Okubo et al.

(10) Patent No.: US 7,094,787 B2
(45) Date of Patent: Aug. 22, 2006

(54) COMPOSITIONS FOR REGULATING DESIRE FOR SMOKING

(75) Inventors: Tsutomu Okubo, Yokkaichi (JP); Makoto Ozeki, Yokkaichi (JP); Takehiko Inden, Yokkaichi (JP); Lekh Raj Juneja, Yokkaichi (JP); Masahiko Hisanabe, Yokkaichi (JP); Ken-ichi Okayama, Osaka (JP)

(73) Assignees: Taiyo Kagaku Co., Ltd., Yokkaichi (JP); Otsuka Chemical Holdings Co., Ltd., Osaka (JP)

( * ) Notice: Subject to any disclaimer, the term of this patent is extended or adjusted under 35 U.S.C. 154(b) by 575 days.

(21) Appl. No.: 10/088,587

(22) PCT Filed: Jul. 18, 2001

(86) PCT No.: PCT/JP01/06202

§ 371 (c)(1),
(2), (4) Date: Mar. 21, 2002

(87) PCT Pub. No.: WO02/07723

PCT Pub. Date: Jan. 31, 2002

(65) Prior Publication Data

US 2003/0003130 A1  Jan. 2, 2003

(30) Foreign Application Priority Data

Jul. 21, 2000  (JP) .............................. 2000-220301
Feb. 9, 2001  (JP) .............................. 2001-34460

(51) Int. Cl.
*A61K 31/505*  (2006.01)
(52) U.S. Cl. .................................... 514/272
(58) Field of Classification Search ................ 514/272; 517/272
See application file for complete search history.

(56) References Cited

U.S. PATENT DOCUMENTS

| 4,634,588 A | * | 1/1987 | Moroe ......................... 424/48 |
| 5,501,866 A | | 3/1996 | Kakuda et al. |
| 5,736,575 A | * | 4/1998 | Kakuda et al. .............. 514/563 |
| 6,132,724 A | * | 10/2000 | Blum ......................... 424/725 |

FOREIGN PATENT DOCUMENTS

| CA | 2320368 A1 | 8/1999 |
| EP | 1 057 483 A1 | 12/2000 |
| EP | 1 275 308 A1 | 1/2003 |
| EP | 1 277 468 A1 | 1/2003 |
| JP | 48-85722 A2 | 11/1973 |
| JP | 57-031620 | 2/1982 |
| JP | 61-063243 | 4/1986 |
| JP | 62-296840 | 12/1987 |
| JP | 04-046119 A | 2/1992 |
| JP | 05-068578 B2 | 3/1993 |
| JP | 05-123166 | 5/1993 |
| JP | 06-100442 A | 4/1994 |
| JP | 6-100442 A | 4/1994 |
| JP | 07-16076 | 1/1995 |
| JP | 08-308544 | 11/1996 |
| JP | 09-12454 A | 1/1997 |
| JP | 9-12454 A | 1/1997 |
| WO | 99/42096 A1 | 8/1999 |

OTHER PUBLICATIONS

Database WPI, XP002263890, Abstract of JP 05-229938A, published Sep. 7, 1993.
Yasuhito Ishimoto et al., The effects of cigarette smoking on the human SEP (Somatosensory Evoked Potential) and EEG, vol. 49, No. 1, (Feb. 25, 1993), pp. 52-70.
Ryohei Kimura et al., Chem. Pharm. Bull., vol. 19, No. 7, (1971), pp. 1301-1307.
Nicotine Dependency Test, Mayumi ABE "Kinengairai," Haga Shoten Tokyo, 1999 (with a copy of pp. 23-24 of the present specification for the translation thereof).

* cited by examiner

*Primary Examiner*—Vickie Kim
(74) *Attorney, Agent, or Firm*—Birch, Stewart Kolasch & Birch LLP

(57) ABSTRACT

An object of the present invention is to provide a composition for suppressing craving for smoking with high safety and no dependence such that there can be performed (1) suppression of craving for smoking in a situation where nonsmoking is mandatory in the daily life; (2) prohibition or moderation of smoking intentionally (when unrestricted); and (3) complete elimination of a smoking habit. Another object of the present invention is to provide a method for prohibiting or moderating smoking comprising administering to an individual the composition comprising theanine.

7 Claims, 10 Drawing Sheets

COMPOSITIONS FOR REGULATING DESIRE FOR SMOKING

This application is the national phase under 35 U.S.C. § 371 of PCT International Application No. PCT/JP01/06202 which has an International filing date of Jul. 18, 2001, which designated the United States of America.

TECHNICAL FIELD

The present invention relates to a composition for suppressing craving for smoking comprising theanine, and a method for prohibiting or moderating smoking comprising administering to an individual the composition comprising theanine.

BACKGROUND ART

Smoking cigarettes has been known to be a major cause of diseases such as a lung cancer, bronchitis, and coronary or peripheral artery disease. Individual chemical substances contained in cigarettes have already been recognized as a carcinogen, and passive smoking has been elucidated to have carcinogenicity recently, so that smokeless chewing tobacco and snuff are also listed in carcinogenic substance list in the United States. Among the components contained in cigarettes, nicotine, which is a colorless volatile liquid alkaloid, has high toxicity of irritating and paralyzing the nerve tissue such as cerebral nerve, cerebellum and spinal cord while having calming effect, excitement effect and pleasure-giving effect. Therefore, there have been continuously reported that nicotine relating to the incidences of lung cancer, pharyngeal cancer, esophageal cancer and gastric cancer.

Nicotine also has mental dependence, so that a continual intake of nicotine by smoking or the like may cause nicotine dependence. For example, when a heavy smoker quits smoking, withdrawal symptoms are seen in a short time period and craving for smoking increases. If the smoker cannot tolerate his craving for smoking, and takes more nicotine to avoid the symptoms and torment, his health is staked at a higher risk.

In those times, campaigns for nonsmoking and moderation in smoking have been run worldwide, and a smoking population tends to be decreased every year. There is a trend toward restriction in smoking in public facilities and public transportation, so that a smoker frequently faces a situation in which he is forced to stop smoking. However, mental and physical torments may be caused by breaking a smoking habit in many cases, and a sudden drop in an intake of nicotine may cause serious withdrawal symptoms. For this reason, there is an earnest need for a method showing an effect on prohibiting or moderating smoking gradually without causing any problems.

As such methods, a food or a medicament such as nicotine gum, and candy, drop or gum, containing various plant extracts, an inorganic substance and the like has been so far known (Japanese Patent Laid-Open No. Sho 4-46119, Japanese Patent Laid-Open No. Sho 61-63243, Japanese Patent Laid-Open No. Sho 62-296840, Japanese Patent Laid-Open No. Sho 62-296840, Japanese Patent Laid-Open No. Hei 8-308544, Japanese Patent Laid-Open No. Sho 82-42582, Japanese Patent Laid-Open No. Hei 7-18076, and Japanese Patent Laid-Open No. Sho 48-85722). Moreover, a method of causing discomfort by inhaling a certain chemical substance simultaneously with cigarette smoke using a pipe or the like, and a method of promoting anti-smoking by absorbing nicotine into body using a nicotine pad or nicotine nasal spray have been used. The principles for prohibiting or moderating smoking by these means are classified into three categories: (1) suppression for craving for smoking by paralyzing gustation and the like; (2) promotion of a detoxification/excretion of nicotine in the body; and (3) supply of nicotine by a cigarette substitute. However, in a case where nicotine is absorbed transdermally or the like, nicotine exists internally after all, so that this method cannot be said to be good for health. Further, even when a reduction in the craving for smoking is achieved, there would be a risk for dependence on the cigarette substitute used. The above-mentioned food or the like has a little effect, and would not satisfactorily gratify smokers' gustation who is generally accustomed to nicotine, so that withdrawal symptoms originated from prohibition or moderation of smoking could not be fundamentally suppressed. Accordingly, it is often the case that a smoker cannot help smoking, so that their effectiveness has a certain limit.

DISCLOSURE OF INVENTION

An object of the present invention is to provide a composition for suppressing craving for smoking with high safety and no dependence such that there can be performed (1) suppression of craving for smoking in a situation where nonsmoking is mandatory in the daily life; (2) prohibition or moderation of smoking intentionally (when unrestricted); and (3) complete elimination of a smoking habit. Another object of the present invention is to provide a method for prohibiting or moderating smoking comprising administering to an individual the composition comprising theanine.

As a result of studies in order to solve the above-mentioned problems, the present inventors have found that theanine is effective for suppressing the craving for smoking, the effectiveness of which is higher than that of the prior art, and that theanine can prevent, alleviate, and eliminate withdrawal symptoms caused by nonsmoking in a situation where nonsmoking is mandatory, and the present invention has been accomplished thereby.

Specifically, the gist of the present invention relates to:

(1) a composition for suppressing craving for smoking, characterized in that the composition comprises theanine; and (2) a method for prohibiting or moderating smoking, comprising administering to an individual a composition comprising theanine.

BRIEF DESCRIPTION OF THE DRAWINGS

FIGS. 2 to 4 are the results of each day of three separate days at which each test is performed.

BEST MODE FOR CARRYING OUT THE INVENTION

Figure 1:
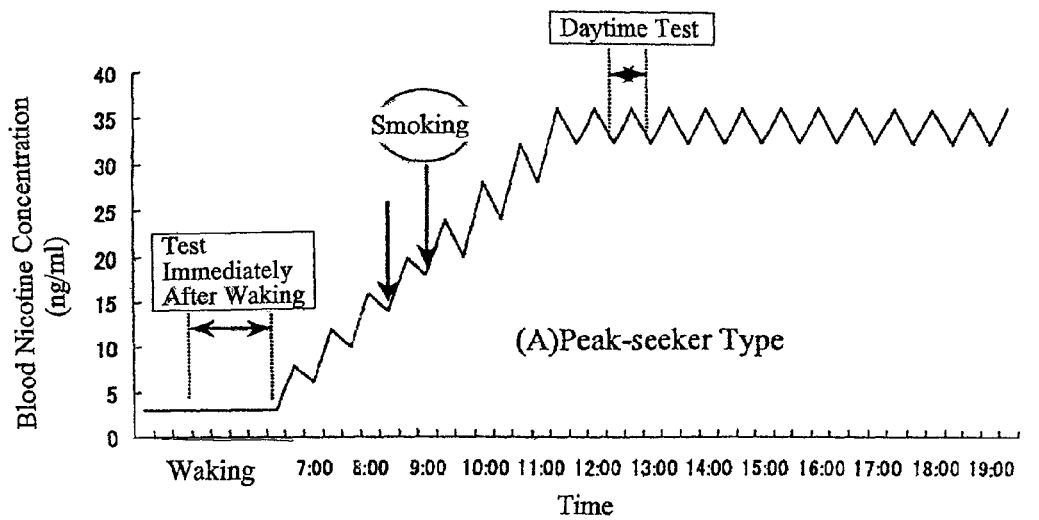
FIG. 1 shows changes in blood nicotine level of a smoker within a day.
Figure 1:
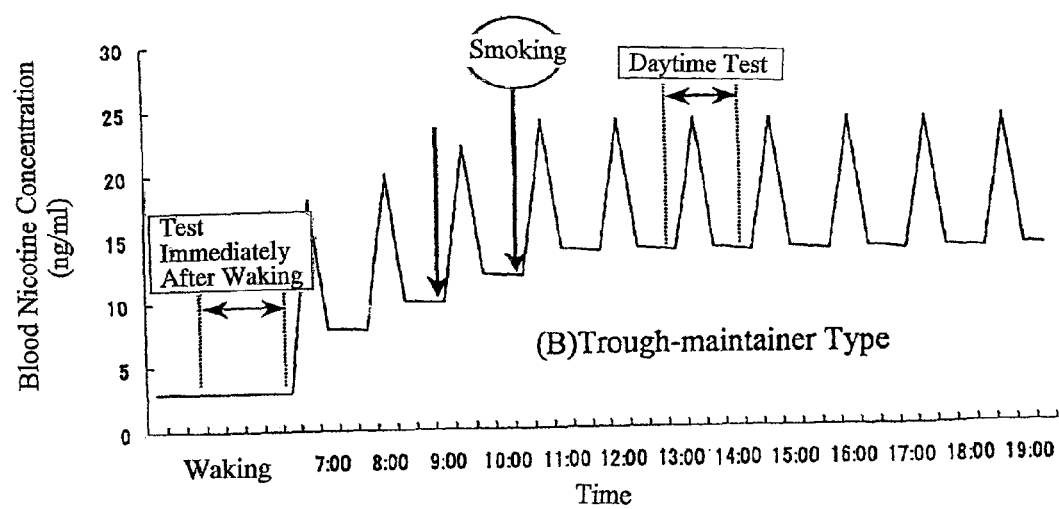

The composition for suppressing craving for smoking (hereinafter referred to as the composition) of the present invention is highly suitable for treating any situations in which cigarette or nicotine-based withdrawal symptoms (hereinafter referred to as withdrawal symptoms) can take place. The exhibition of the desired effects of the composition of the present invention is based on action for suppressing the craving for smoking found for the first time in theanine contained in the composition.

The phrase "suppressing craving for smoking" refers to, for example, alleviating withdrawal symptoms and suppressing an onset of the withdrawal symptoms, thereby suppressing craving for smoking.

The term "nicotine" refers to an active ingredient in tobacco products. It has been known that nicotine is a dependence-producing drug and is easily absorbed internally and reaches the brain after about eight seconds. Nicotine affects the pleasure center of cerebrum (central nervous system) to provide pleasure. If one continues smoking for craving the pleasure, so-called cigarette or nicotine dependence may occur, wherein certain changes take place in the brain, and body conditioning gets worse in a case of non-smoking.

On the other hand, "theanine" used in the present invention is a glutamic acid derivative (γ-glutamyl ethylamide), and is an amino acid ingredient contained largely in tea leaves naturally. Although an action mechanism of the action for suppressing the craving for smoking by theanine found for the first time in the present invention is yet unknown and not expected from various physiological functions conventionally known, as shown in Examples set forth below, there has been acknowledged association between the changes in the theanine blood concentration after theanine administration and the exhibition of suppressive action of withdrawal symptoms from the results of tests conducted for smokers with nicotine dependence. Therefore, the transfer of theanine into the brain after the administration would have some association with the exhibition of the effect.

Methods for preparing theanine used in the present invention may be any of known methods, including a method of extracting from tea leaves; a method for obtaining theanine by an organic synthesis method [*Chem. Pharm. Bull.*, 19(7), 1301–1307 (1971)]; a method for obtaining theanine, comprising treating a mixture of glutamine and ethylamine with glutaminase (Japanese Examined Patent Publication No. Hei 7-55154); a method comprising culturing cultured cells of tea in a medium containing ethylamine, thereby achieving growth promotion of the cultured cells while increasing the cumulative amount of theanine in the cultured cells (Japanese Patent Laid-Open No. Hei 5-123166); a method for obtaining theanine in which ethylamine is substituted by an ethylamine derivative such as ethylamine hydrochloride in the above-mentioned method disclosed in Japanese Examined Patent Publication No. Hei 7-55154 or Japanese Patent Laid-Open No. Hei 5-123166; and the like. In addition, the theanine used in the present invention may be of any forms, such as purified products, crudely purified products, extracts, and the like. Also, a commercially available product [SUNTHEANINE (registered trade mark), manufactured by Taiyo Kagaku Co., Ltd.] may be used. Incidentally, the term "tea leaves" as referred to herein include those of green tea, oolong tea and black tea.

In addition, any of L-theanine, D-theanine and DL-theanine can be used, among which the L-form is preferred in the present invention, because it is approved as a food additive, and is economically utilizable.

The theanine content in the composition of the present invention is not particularly limited, as long as the desired effect of the present invention is achieved. The theanine content is usually preferably from 0.001 to 100% by weight, more preferably from 0.01 to 100% by weight, and especially preferably from 0.1 to 100% by weight.

A method of detecting theanine in the composition of the present invention is not particularly limited. It is preferable that the method comprises derivatizing in pre-column by orthophthalaldehyde (OPA), separating by high-performance liquid chromatography (HPLC) using ODS column, and detecting and quantifying with a fluorescence detector, or the method comprises separating by HPLC using ODS column, and detecting and quantifying at a wavelength of 210 nm.

In addition, other various components can be used together with theanine in the composition of the present invention properly. The other components are not particularly limited, and include, for instance, amino acids, vitamins, minerals, other functional materials and the like.

The above-mentioned amino acids are not particularly limited, and include, for example, glutamine, glutamic acid, tryptophan, alanine, arginine, aspartic acid, threonine, serine, γ-aminobutyric acid, taurine, tiotaurine, hypotaurine, and the like.

The above-mentioned vitamins include, for example, vitamin A, vitamin $B_1$, vitamin $B_2$, vitamin $B_6$, vitamin $B_{12}$, vitamin C, vitamin D, vitamin E, vitamin K, folic acid, nicotinic acid, lipoic acid, pantothenic acid, biotin, ubiquinone, prostaglandin and the like, and derivatives of these vitamins, without intending to be limited to these alone.

The above-mentioned minerals include, for example, calcium, iron, magnesium, copper, zinc, selenium, potassium and the like, without intending to be limited thereto.

Moreover, the above-mentioned other functional materials include, for example, St. John's wort, herbs such as Chamomile, Gymnema/Garcinia, plants pertaining to Chinese-style medicine such as Eucommia ulmoides and Pnanx ginnseng or extracts thereof, extracts of animal origins such as placenta, dietary fiber, soy peptide, diet sweetener, caffeine and the like, without intending to be limited thereto.

As the form of the composition of the present invention, a food composition or a pharmaceutical composition is preferable, from the viewpoint of its suitability for the daily use.

The food composition of the present invention encompasses not only a food comprising theanine but also a food additive comprising theanine. In the case of making the food composition, theanine may be added to, for example, the following foods.

Specifically, theanine can be added to a solid food or a liquid food. The solid food is not particularly limited, and preferably includes tablet confectioneries, candies, chocolates, gum, crackers, biscuits, cookies, paste products, processed soy products, mousse, jelly, yogurt, cold confectioneries, cake, bread and the like. The liquid food is also not particularly limited, and theanine may be preferably added to a table luxury beverage such as fruit juice concentrates, reconstituted juice concentrates, fresh juices, mixed fruit juices, fruit grain-containing fruit juice, fruit juice-containing beverages, mixed fruit/vegetable juice, vegetable juice, carbonated beverages, soft drinks, mineral water, milk, milk beverage and coffee, or an alcoholic beverage such as Japanese sake, beer, wine, cocktails, shochu, and whiskey, or the like.

Among them, a preparation suitable for absorption via the oral mucosa is preferred. For instance, a solid food in the form which can be sustained in the mouth for a given length of time, such as a tablet confectionery, a candy or gum, is especially preferred. In the case of the solid food, theanine can be gradually released in the mouth. By that action, theanine is absorbed internally via mainly the oral mucosa. When theanine is absorbed via the oral mucosa, theanine would be transported into the brain more efficiently than the case through the portal system, whereby its action can be exhibited. On the other hand, when considering oral intake, since it may be difficult to use gum depending on the kind of an occupation and a situation of a workplace, the form of tablet confectionery or candy is more preferable. With respect to these various forms, as those suitable for absorption via the oral mucosa, a dosage form sustainable in the mouth for at least three minutes when orally taken is preferred. Moreover, the size and the form are preferably those which would be difficult to chew down and swallow.

In the case of making the composition of the present invention into a pharmaceutical composition, its form, which is based on known pharmaceutical compositions, may be any of solutions, suspensions, powders, solid molded products and the like without being particularly limited thereto. Therefore, the pharmaceutical composition is provided as tablets (including not only general tablet but also troche and the like), capsules, powdered agents, granules, health care drinks and the like. The pharmaceutical composition can also be used in combination with other medicaments.

Moreover, as in the case of the food composition, those suitable for absorption via the oral mucosa are preferred. Accordingly, from the viewpoint of absorbing theanine internally without mediating portal system, as the form of the pharmaceutical composition of the present invention, tablets, especially troche or a sublingual tablet, are preferred. The sublingual tablet is not particularly limited, as long as the tablet can be placed under the tongue. It is desirable that the tablet preferably disintegrates in three to six minutes, whereby theanine can be released to sublingual mucosa rapidly. The means for disintegration is not particularly limited, and may follow a conventional method. By the use of the sublingual tablet, theanine is absorbed via sublingual mucosa and can be efficiently transported into the brain, so that the sublingual tablet is especially suitable for the treatment of acute withdrawal symptoms or the treatment of transient nicotine craving.

A process for preparing the composition of the present invention is not particularly limited, and there can be used general processes for preparation of a food and a medicament such as a process of powder-mixing theanine and other raw materials; a process of dissolving theanine and other raw materials in a solvent to give a mixed solution; and a process of freeze-drying the mixed solution; a process of spray-drying the mixed solution. For example, a pharmaceutical composition can be prepared by mixing theanine with a vehicle, a carrier, a binder, a stabilizer and the like, which are known in the art.

By the use of the composition of the present invention, there can be performed, for instance, (1) the suppression of craving for smoking in a situation where nonsmoking is mandatory in the daily life. For an individual having a smoking habit who does not wish to eliminate the habit of smoking, it may be very difficult to quit smoking for a given period of time, whether short or long. The situation where nonsmoking is mandatory includes, for example, the situation during the use of public transportations such as air planes and the situation in a hospital. In these cases the craving for smoking can be suppressed efficiently by the use of the composition of the present invention so that smoking can be stopped without causing any problems. However, the suppressive action is not persistent unnecessarily for a long period of time, and smoking can be restarted easily once the period of time where nonsmoking is mandatory has passed. Such a flexibility of suppressing the craving for smoking and restarting smoking is very excellent aspect as compared to the suppression of the craving for smoking by conventional nicotine substitute such as nicotine pad which may unnecessarily sustain the suppressive effect for the craving for smoking. Particularly in recent years, there is an increase in a situation where nonsmoking is mandatory along with the progress of understanding about harmful action of cigarette consumption and nicotine intake accompanied therewith, so that the embodiment of the use of the composition of the present invention mentioned above is especially preferred.

Moreover, there can be performed (2) prohibition or moderation of smoking intentionally (when unrestricted) by using the composition of the present invention. When an individual having a habit of smoking who does not wish to eliminate the habit tries to stop or moderate smoking under a direction of a physician, when an individual tries to stop smoking during the contact with an infant, or the like, the craving for smoking can be suppressed efficiently by using the composition of the present invention, so that smoking can be stopped or moderated without causing any problems. In addition, in the same manner as mentioned above, in a case where intentional prohibition or moderation for smoking is no longer necessary, smoking cigarettes can be restarted at once.

Further, there can be performed (3) complete elimination of a smoking habit by taking the composition of the present invention continuously. It is said that there are generally a few individuals having confidence about quitting smoking among smokers who are starting to stop smoking. This is especially true when an individual had given up on quitting smoking in some of past challenges due to painful withdrawal symptoms after starting to quit smoking. However, since the craving for smoking can be suppressed efficiently by using the composition of the present invention, nonsmoking can be continued without causing any problems, and finally, the smoking habit can be completely eliminated.

Moreover, by using the composition under the appropriate instruction or counseling for quitting smoking, a further effect can be expected. Hitherto, in the instruction or the like, nicotine preparations such as nicotine gum and nicotine pad have been used as anti-smoking supplement. However, nicotine is highly toxic and is contraindicated in individuals with unstable angina, individuals with myocardial infarction, gravida, women who are possibly pregnant and the like. The above-mentioned anti-smoking supplement should be prescribed for the purpose that an individual who intends to stop smoking may use it by himself under a proper direction. If another individual uses the anti-smoking supplement, it is not necessarily safe. Particularly, in the case of passing the anti-smoking supplement to the contraindicative individual by hand-over, there has been a possibility of causing a situation with risk. Moreover, a nicotine preparation serves as a temporary substitute of source of nicotine, which had been taken from cigarettes, so that dependence to the nicotine preparation may take place.

Since the theanine used in the composition of the present invention is completely safe component as mentioned below and has no possibility of theanine dependence, an addictive smoker can eliminate the smoking habit safely and effectively by the use of the composition under the direction for quitting smoking.

As described above, by the use of the composition of the present invention, since withdrawal symptoms caused by prohibition or moderation of smoking can be prevented, alleviated or eliminated, the above-mentioned various embodiments of use can be made.

Further, the present invention provides a method for prohibiting or moderating smoking, comprising administering to an individual (human) a composition comprising theanine. In the method, the use of the composition of the present invention is preferred. An effective dose of theanine in order to obtain the desired effect of the present invention in the above-mentioned embodiment of use of the composition of the present invention is, generally, preferably from 0.1 to 50 mg/kg weight per day, more preferably from 0.5 to 20 mg/kg weight, still more preferably from 1 to 20 mg/kg weight, especially preferably from 4 to 20 mg/kg weight.

The timing of using the composition of the present invention is not particularly limited. For instance, the composition may be previously administered when withdrawal symptoms are presumed to be caused by prohibition or moderation for smoking, or may be administered during occurrence of withdrawal symptoms. In a more specific embodiment, when a smoker wishes to temporarily treat withdrawal symptoms, the composition is administered to the smoker before or during the experience of withdrawal symptoms, the smoker being preferably a smoker who cannot help smoking during cigarette- or nicotine-deficient state for a long period of time, for instance, a smoker who has a habit of smoking within fifteen minutes from the point of waking. The smoker is administered in an effective dose per dosage of the theanine sufficient to suppress the craving for smoking, for instance, upon waking, which is preferably from 0.02 to 10 mg/kg weight, more preferably from 0.2 to 10 mg/kg weight, still more preferably from 0.8 to 10 mg/kg weight. On the other hand, when a smoker wishes to completely eliminate the smoking habit, it is desirable to administer an effective dose per dosage of the theanine sufficient to suppress the craving for smoking preferably for at least three hours or so, more preferably for five hours or so, for instance, upon beginning of the craving for smoking, which is preferably from 0.02 to 10 mg/kg weight, more preferably from 0.2 to 10 mg/kg weight, still more preferably from 0.8 to 10 mg/kg weight.

However, since there are differences (e.g. age, gender) between individuals in a level of smoking habit or withdrawal symptoms, the dosage of theanine in the present invention is not particularly limited to the above range. The dosage of theanine is may be properly adjusted depending upon each smoker's state and a desired effect level. Also, the number and interval of administration can be properly selected.

Further, as another embodiment of the present invention, the present invention provides use of theanine for preparing a medicament for preventing, alleviating or eliminating withdrawal symptoms caused by prohibition or moderation of smoking.

The composition of the present invention is based on action for suppressing the craving for smoking that has been found for the theanine for the first time. The theanine has been known to be a main ingredient of sapidity in tea and used as a food additive for the sapidity. As to its safety, there is no case of death in acute toxicity test using mice with oral administration at 5 g/kg weight, and there is no abnormality in the general state and body weight. There is no limitation in an amount of addition based on the Food Hygiene Law. Further, unlike a conventional nicotine preparation, since there is no dependence, the composition of the present invention can suppress the craving for smoking safely and effectively.

EXAMPLES

Next, the present invention will be further described by means of Examples and Test Examples, without intending to limit the scope of the present invention to these Examples alone.

Production Example 1

Preparation of L-Theanine by Enzymatic Method 0.3 M glutamine and 1.5 M ethylamine were allowed to react at 30° C. for 22 hours in borate buffer ($Na_2B_4O_7$—NaOH, pH 11) in the presence of 0.3 U glutaminase, to give 225 nmol of L-theanine. In addition, a by-product glutamic acid was 20 nmol. The purification of theanine from the reaction mixture was carried out by subjecting the reaction mixture to column chromatography using Dowex 50×8 column and Dowex 1×2 column, and thereafter treating the resulting product with ethanol.

First, L-theanine was identified by subjecting the isolated substance obtained by the above-mentioned purification to amino acid analyzer and paper chromatography, whereby confirming that the isolated substance exhibits the same behaviors as the standard substance. Moreover, when the isolated substance was subjected to hydrolysis treatment with hydrochloric acid or glutaminase, glutamic acid and ethylamine were generated at a ratio of 1:1. Since the isolated substance was hydrolyzed by glutaminase, it was shown that ethylamine was bonded at the γ-position of glutamic acid. In addition, it was also confirmed by using the glutamic acid dehydrogenase that glutamic acid generated by hydrolysis had an L-form. From the above, the resulting compound was finally confirmed to be L-theanine.

Production Example 2

Extraction of L-Theanine from Tea Leaves

Ten kilograms of tea leaves (*Camellia sinensis L.*) were subjected to extraction with boiling water. The resulting extract was then applied to a cationic exchange resin ("Dowex HCR W-2," manufactured by Muromachi Kagaku Kogyo K.K.), and eluted with 1 N NaOH. The eluted fraction was applied to an activated carbon ("Taiko Kasseitan SG" manufactured by Futamura Kagaku Kogyo K.K.), and eluted with 15% ethanol. The resulting eluted fraction was concentrated with an RO membrane (manufactured by NITTO DENKO CORPORATION "NTR 729 HF"). Thereafter, the concentrate was purified by column chromatography. Furthermore, the purified product was recrystallized, to give 24.8 g of L-theanine.

Example 1

Preparation of L-Theanine Formulated Chewable Tablet

As one example of an L-theanine formulated composition for suppressing craving for smoking, the raw materials given below were mixed in accordance with each composition, and the mixture was granulated. Thereafter, the granulated product was tableted to be 1.5 g per each tablet, to prepare an L-theanine formulated chewable tablet.

| | | |
|---|---|---|
| Frosted Sugar | 71.67% by weight | (1.075 g) |
| Trehalose | 10.00% by weight | (0.150 g) |
| L-Theanine ("SUNTHEANINE" manufactured by Taiyo Kagaku Co., Ltd.) | 13.33% by weight | (0.200 g) |
| Sucrose Fatty Acid Ester | 1.00% by weight | (0.015 g) |
| Flavor (manufactured by TAKASAGO INTERNATIONAL CORPORATION) | 4.00% by weight | (0.060 g) |
| Total | 100% by weight | (1.500 g) |

Example 2

Preparation of L-Theanine Formulated Chewable Tablet

As one example of an L-theanine formulated composition for suppressing craving for smoking, the raw materials given below were mixed in accordance with each composition, and the mixture was granulated. Thereafter, the granulated product was tableted to be 1.5 g per each tablet, to prepare an L-theanine formulated chewable tablet.

| | | |
|---|---|---|
| Frosted Sugar | 68.34% by weight | (1.025 g) |
| Trehalose | 10.00% by weight | (0.150 g) |
| L-Theanine ("SUNTHEANINE" manufactured by Taiyo Kagaku Co., Ltd.) | 13.33% by weight | (0.200 g) |
| Caffeine | 3.33% by weight | (0.050 g) |
| Sucrose Fatty Acid Ester | 1.00% by weight | (0.015 g) |
| Flavor (manufactured by TAKASAGO INTERNATIONAL CORPORATION) | 4.00% by weight | (0.060 g) |
| Total | 100% by weight | (1.500 g) |

Example 3

Preparation of L-Theanine Formulated Chewing Gum

As one example of an L-theanine formulated composition for suppressing craving for smoking, the raw materials given below were mixed in accordance with each composition, to prepare chewing gum.

| | | |
|---|---|---|
| Gum Base | 20.0% by weight | (0.7 g) |
| Grinded Sugar | 74.3% by weight | (2.6 g) |
| L-Theanine ("SUNTHEANINE" manufactured by Taiyo Kagaku Co., Ltd.) | 5.7% by weight | (0.2 g) |
| Total | 100.0% by weight | (3.5 g) |

The above-mentioned raw materials were mixed and kneaded until the mixture became homogeneous. The resulting kneaded product was extruded with an extruder into a sheet-like form, with keeping the temperature at 50° C., and further pressed with a pressure roller into a sheet having a given thickness. The sheet was cut into a size of 20 mm×75 mm, to produce L-theanine formulated chewing gum of 3.5 g per piece.

Example 4

Preparation of L-Theanine Formulated Granule

As one example of an L-theanine formulated composition for suppressing craving for smoking, there were mixed lactose (50 g), L-theanine (10 g), caffeine (3 g), flavor (2 g, manufactured by TAKASAGO INTERNATIONAL CORPORATION), vitamin C (15 g) and starch (20 g), and granulated, to prepare an L-theanine formulated granule, so that each granule was packed and wrapped to be 2 g per package.

Example 5

Preparation of L-Theanine Formulated Powdery Beverage

As one example of an L-theanine formulated composition for suppressing craving for smoking, there were mixed powdered green tea (50 g), L-theanine (10 g), grinded sugar (20 g), vitamin C (10 g) and citric acid (1 g), and granulated, to prepare L-theaninie formulated powdery beverage, so that each powdery beverage was packed and wrapped to be 2 g per package.

Example 6

Preparation of L-Theanine Formulated Chocolate

As one example of an L-theanine formulated composition for suppressing craving for smoking, there were mixed cacao mass (60 g), L-theanine (0.5 g), trehalose (9 g), glycerol fatty acid ester (0.9 g), whole powdered milk (10 g), and vegetable oil (10 g), to prepare L-theanine formulated chocolate by a conventional method.

Example 7

Preparation of L-Theanine Formulated Beverage

As one example of an L-theanine formulated composition for suppressing craving for smoking, fructose (10 g), muscat fruit juice (1 g), vitamin C (2 g), L-theanine (0.4 g), and citric acid (1 g) were dissolved in 1 liter of water. The resulting mixture was filled in a can so as to be 350 g per can, and thereafter sterilized, to prepare an L-theanine formulated beverage.

Comparative Example 1

Preparation of Control Chewable Tablet

The raw materials given below were mixed in accordance with each composition, and the mixture was granulated. Thereafter, the granulated product was tableted so as to be 1.5 g per each tablet, to prepare a control chewable tablet.

| | | |
|---|---|---|
| Frosted Sugar | 85.00% by weight | (1.275 g) |
| Trehalose | 10.00% by weight | (0.150 g) |
| Sucrose Fatty Acid Ester | 1.00% by weight | (0.015 g) |
| Flavor (manufactured by TAKASAGO INTERNATIONAL CORPORATION) | 4.00% by weight | (0.060 g) |
| Total | 100% by weight | (1.500 g) |

Comparative Example 2

Preparation of Control Chewing Gum

The raw materials given below were mixed in accordance with each composition, to prepare a control chewing gum.

| | | |
|---|---|---|
| Gum Base | 20.0% by weight | (0.7 g) |
| Grinded Sugar | 80.0% by weight | (2.8 g) |
| Total | 100.0% by weight | (3.5 g) |

The above-mentioned raw materials were mixed and kneaded until the mixture became homogeneous. The resulting kneaded product was extruded with an extruder into a sheet-like form, with keeping the temperature at 50° C., and further pressed with a pressure roller into a sheet having a given thickness. The sheet was cut into a size of 20 mm×75 mm, to produce a control chewing gum of 3.5 g per piece.

Test Example 1

Nicotine Dependency Calming Test (1) Selection of Subjects

In order to select subjects with high nicotine dependency, volunteer smokers were subjected to nicotine dependency test (Mayumi ABE, "Kinengairai," Haga Shoten, Tokyo, 1999) developed by Dr. Fagerström shown in Table 1.

TABLE 1

| Question | Answer | Scores |
|---|---|---|
| After how many minutes do you make a first puff after waking? | Within 30 min. | 1 |
| | 30 min. or more | 0 |
| Do you find it very difficult to refrain from smoking in the facilities which prohibit smoking such as nonsmoking cars, libraries, and movie theaters? | Yes | 1 |
| | No | 0 |
| Which puff is most difficult to quit? | First puff in the morning | 1 |
| | Others | 0 |
| How many cigarettes do you smoke per day? | 15 or less | 0 |
| | 16–25 | 1 |
| | 26 or more | 2 |
| Do you smoke more cigarettes in the morning? | Yes | 1 |
| | No | 0 |
| Do you smoke even when you are ill and stay in bed a whole day long? | Yes | 1 |
| | No | 0 |
| What is the nicotine content of the cigarette which you usually smoke? | 0.9 mg or less | 0 |
| | 1.0–1.2 mg | 1 |
| | 1.3 mg or more | 2 |
| Do you inhale deeply? | Not at all | 0 |
| | Sometimes | 1 |
| | Always | 2 |

The level of the nicotine dependency was judged in accordance with the following evaluation criteria by totaling the scores in the above-mentioned test:

Evaluation Criteria 0 to 3 points: low level of dependency:

4 to 5 points: moderate level of dependency 6 or more points: high level of dependency (2) Short-Term Nicotine Dependency Calming Test If smokers are classified by the changes of the blood nicotine concentration within one day, as shown in FIG. 1, the smokers can be classified into (A) Peak-seeker Type and (B) Trough-maintainer Type. The Peak-seeker Type smokers are largely seen in so-called "heavy smokers," who keep on puffing in order to avoid the lowering of the blood nicotine level. The nicotine in the body is accumulated, and reaches a given level by the afternoon. On the other hand, the Trough-maintainer Type smokers are those who seek for smoking stimulation periodically, and the number of cigarettes which they smoke is small. The peak of the blood nicotine concentration is clearly found. In this test, in order to study on the suppressive effect of craving for smoking by theanine, a test was conducted in a state of immediately after waking, at which body nicotine concentration is the lowest (Tests 1 and 2 Immediate After Waking). Further, as is seen in the Peak-seeker Type smokers, a test was conducted in the afternoon at which the nicotine concentration presumably reaches the highest level during the day (Daytime Test). Also, an effect of continuous intake within a day was also studied. Specifically, it was studied whether or not a time period until a smoker makes a first puff after waking can be significantly extended by an intake of theanine, whether or not the interval of puffing during the day can be significantly extended by the intake, and whether or not the number of cigarettes which they smoke are significantly decreased by the intake.

(i) Test 1 Immediately After Waking

1) Test

Fifty of those subjects which had a dependency of moderate level or higher in item (1) above, and habit of smoking within 15 minutes from waking (average body weight: 73 kg) were selected as subjects, and subjected to a test. In the test, a test substance listed in Table 2 was taken immediately after waking (within about 15 minutes after waking), and they recorded a time period from the intake of the test substance to a first puff (pre-smoking time period) was studied.

The subjects were divided into 5 groups (10 persons per group), and each subject was allowed to take any of the test substances in Table 2 assigned to each group every day from Monday to Friday, and the pre-smoking time period was determined. Based on the data of the obtained pre-smoking time period, the average time period was determined for each test substance, each of which was shown in Table 2 as the pre-smoking time period.

During the test period, each of the subjects was not informed which of the test substances the subjects were allowed to take. During the test period, there were no restriction on their life including smoking, except for the intake of the test substance immediately after waking.

TABLE 2

| Test Substance | Pre-Smoking Time Period |
| --- | --- |
| L-Theanine Formulated Chewable Tablet of Example 1 | 3 hours ± 30 minutes |
| L-Theanine Formulated Chewable Tablet of Example 2 | 3 hours ± 30 minutes |
| L-Theanine Formulated Chewing Gum of Example 3 | 2.5 hours ± 30 minutes |
| Control Chewable Tablet of Comparative Example 1 | 40 minutes ± 15 minutes |
| Control Chewing Gum of Comparative Example 2 | 40 minutes ± 15 minutes |

2) Results

As shown in Table 2, in the group with the intake of the test substance of Comparative Examples 1 and 2, the pre-smoking time period was short, and thus a suppressive effect for craving of smoking could not be found. On the other hand, in the group with the intake of the test substances of Examples 1 to 3 formulated with theanine, the time period until making a first puff after the intake of the test substance is remarkably extended, and thus a suppressive effect for craving of smoking could be found.

(ii) Test 2 Immediately After Waking

1) Subjects

A preliminary questionnaire was conducted to the subjects in accordance with the nicotine dependency test of item (1) above, and 23 subjects having a moderate level or higher dependency (average body weight: 68 kg) were selected. The subjects were males of ages from 31 to 59, having a smoking career of 10 to 40 years.

2) Preliminary Questionnaire

Prior to carrying out the test, the subjects were asked to record the smoking time in the questionnaire chart during a period of waking to sleep over two days each for holidays and working days, and (1) the number of cigarettes smoked/day, (2) a time period until making a first puff after waking, and (3) an average smoking time interval were previously surveyed.

3) Test

As the theanine, L-theanine (trade name "SUNTHEANINE," manufactured by Taiyo Kagaku Co., Ltd.) of a food additive grade (purity: 99% or more) was used. The compositions of the test substance (Example 8) and the placebo (Comparative Example 3) are shown in Table 3. The content of theanine was 200 mg, and lactose was substituted for the theanine in the placebo. The shape was a troche-like tablet (φ15 mm×7 mm) in order to sustain the tablet in the mouth for about 5 minutes.

TABLE 3

| Composition of Test Substance and Placebo | | |
| --- | --- | --- |
| Raw Materials | Test Substance | Placebo |
| Sucrose | 1.015 g | 1.015 g |
| Trehalose | 0.150 g | 0.150 g |
| L-Theanine ("SUNTHEANINE" manufactured by Taiyo Kagaku Co., Ltd.) | 0.200 g | 0.000 g |
| Lactose | 0.000 g | 0.200 g |
| Lubricant (Polyglycerol Fatty Acid Ester) | 0.015 g | 0.015 g |
| Flavor Powder Form | 0.120 g | 0.120 g |
| Total | 1.500 g | 1.500 g |

Two tablets of the test substance and 2 tablets of the placebo were given out to each subject, and the subject was asked to take one tablet per day in a designated order to conduct a test for a total of four days according to the double-blind method. Each of the test substance and the placebo was taken within 15 minutes after waking. The subjects were asked to refrain from smoking after the intake until a moment at which craving for smoking could no longer be suppressed. The subjects were asked to record the waking time, the intake time of the test substance or the placebo, and the entire smoking time during the day in the questionnaire chart.

4) Results

Figure 2:
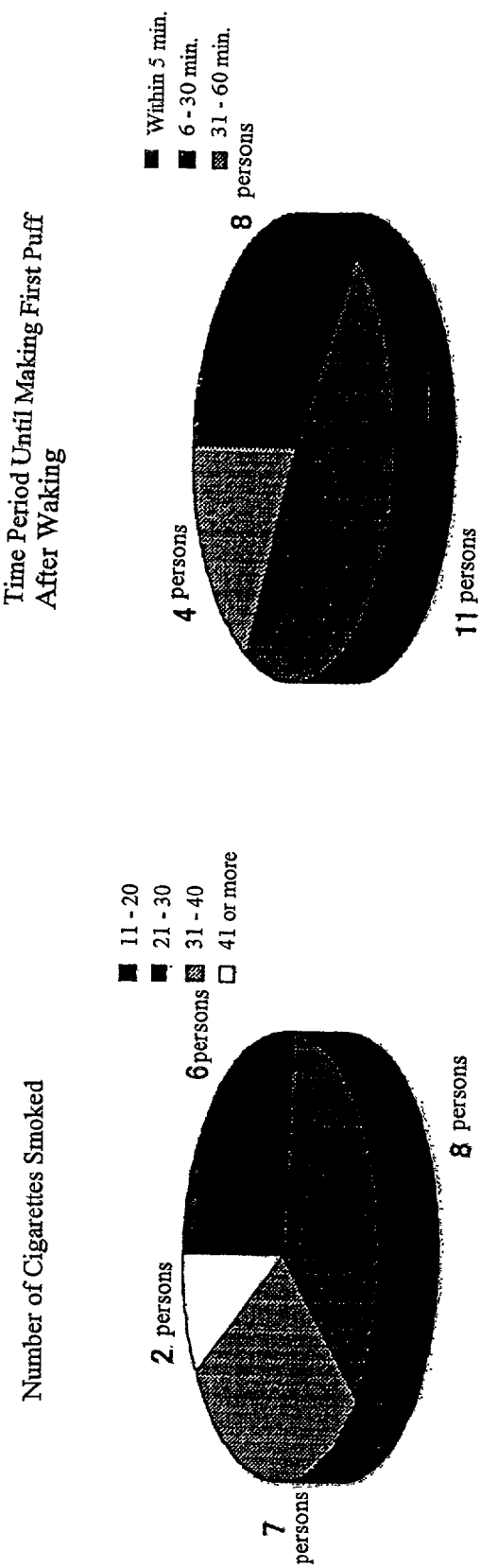
FIG. 2 shows the results of the preliminary questionnaire of Test 2 immediately after waking.

The results for the preliminary questionnaire of the number of cigarettes smoked and the time period until making a first puff after waking for 23 subjects are shown in FIG. 2. About 74% of the subjects smoked 21 or more cigarettes per day, and about 83% of the subjects started a first puff of the day within 30 minutes after waking. This group was deduced to be a group which is relatively strongly nicotine-dependent.

Figure 3:
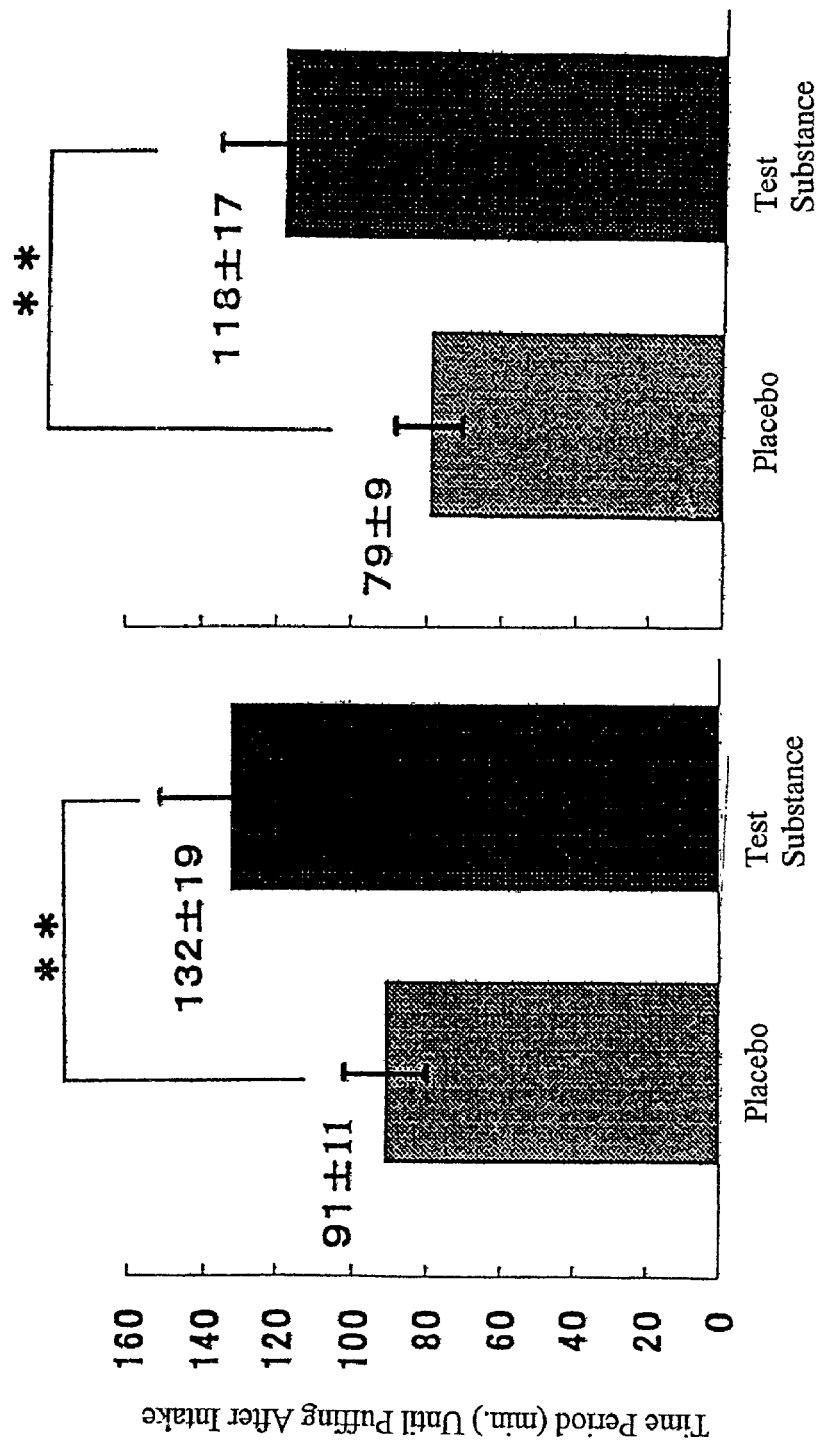
FIG. 3 shows the results of Test 2 immediately after waking.

The test results are shown in FIG. 3. The test was carried out for two groups: the group of the entire subjects and the group of the subjects smoking within 30 minutes after waking. The test substance containing theanine had a greater smoking suppressive effect than that of the placebo, showing that a smoking suppressive effect was 2 hours or longer after the intake. The placebo group and the test substance group each showed a statistically significant difference. Here, the test was carried out by Student paired t-test.

(iii) Daytime Test

1) Subjects

As the subjects, 39 subjects were selected (average body weight: 70 kg) from the same participants as those of item (ii) Test 2 Immediately After Waking above. The subjects were of ages from 26 to 59, having a smoking career of 3 to 40 years, including one female.

2) Preliminary Questionnaire

Prior to carrying out the test, a preliminary questionnaire was conducted in the same manner as that of item (ii) Test 2 Immediately After Waking above.

3) Test

As theanine, a test substance and placebo, the same ones as those in item (ii) Test 2 Immediately After Waking above were used. The test was carried out for a total of four working days which had no business trip or even a brief going-out-on business.

Two tablets of the test substance and 2 tablets of the placebo were given out to each subject, and the subject was asked to take the tablet in a designated order to conduct a test according to the double-blind method. During the morning of the testing day, the subjects were allowed to smoke freely. Each of the test substance and the placebo was taken within 30 minutes from the last puff before starting the afternoon work, and the subjects were asked to refrain from smoking until a moment at which craving for smoking could no longer be suppressed. The subjects were asked to record the smoking time during the morning, the intake time of the test substance or the placebo, and all the smoking time in the afternoon in the questionnaire chart.

4) Results

Figure 4:
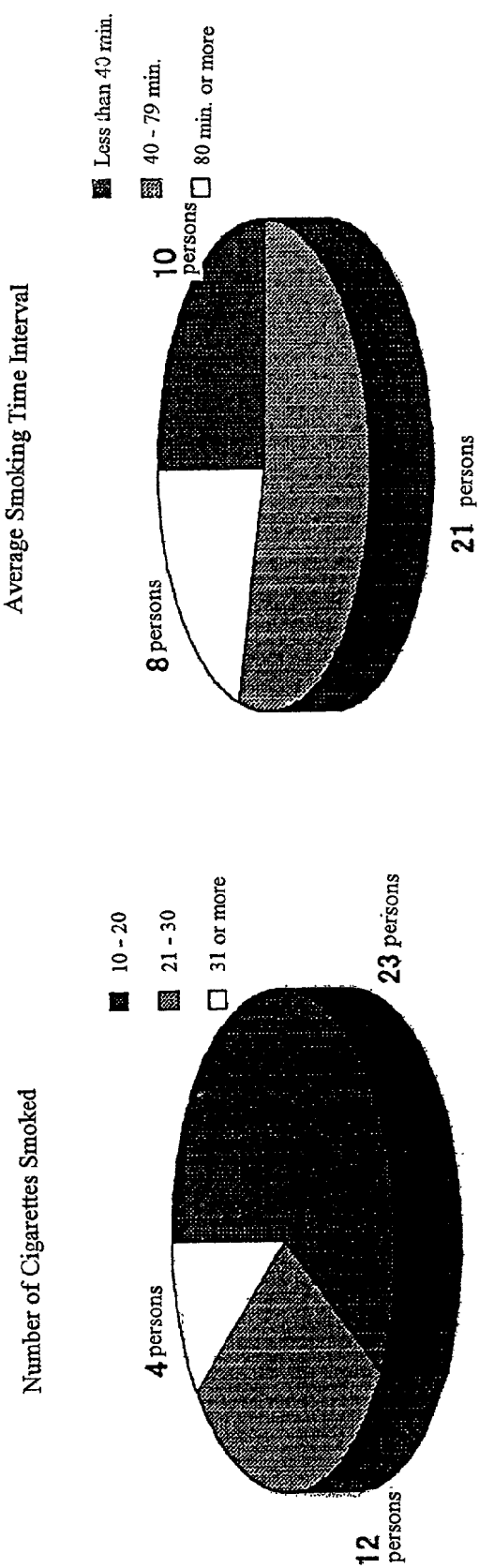
FIG. 4 shows the results of the preliminary questionnaire of the daytime test.
Figure 5:
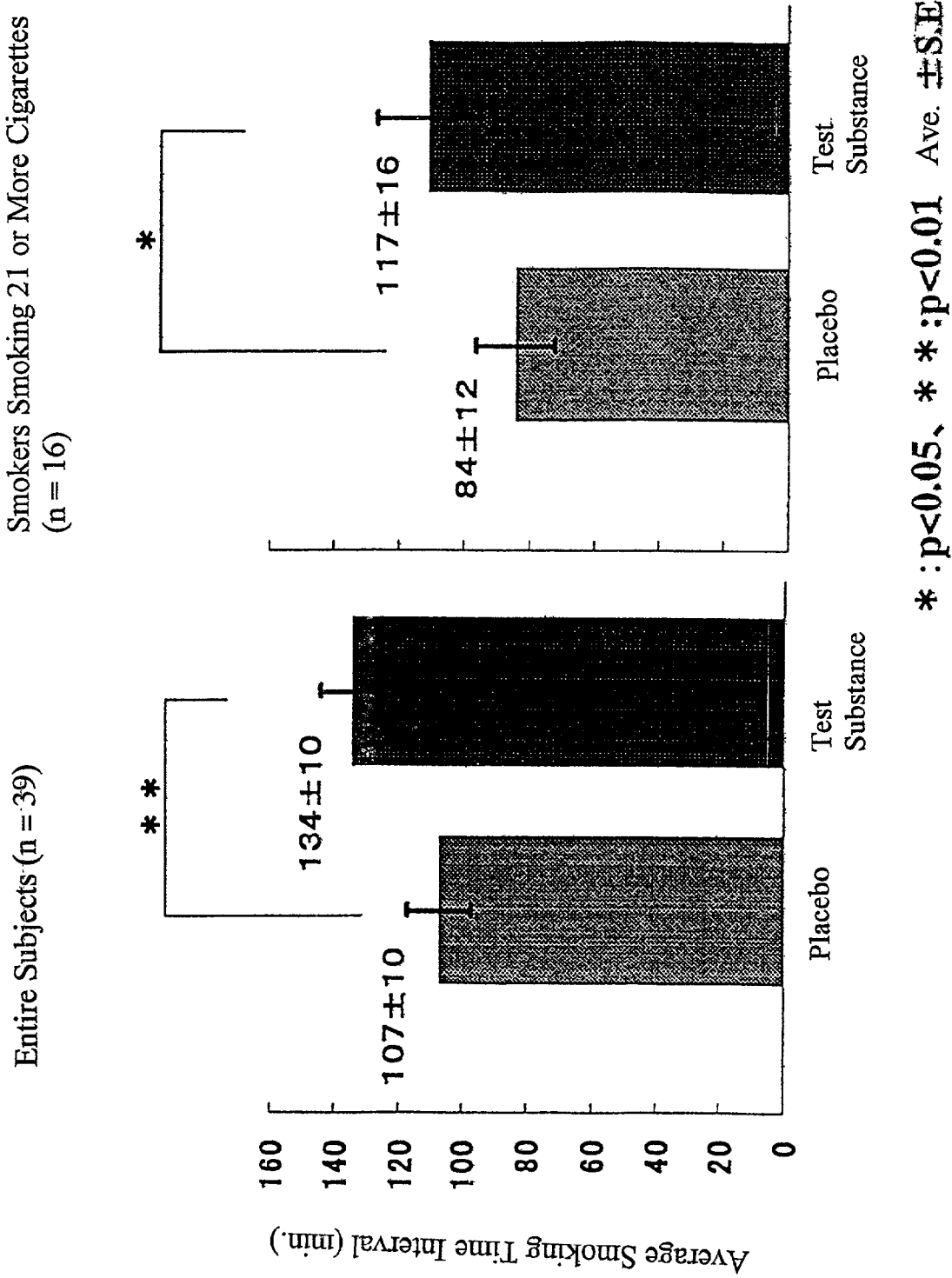
FIG. 5 shows the results of the daytime test.

The preliminary questionnaire results of the number of cigarettes smoked and the average smoking time interval for 39 subjects participated in the daytime test are shown in FIG. 4. The number of cigarettes smoked per day ranged from the level of 10 to 40. Therefore, this test was carried out for two groups: the group of the entire subjects and the group of the relatively strongly nicotine-dependent subjects smoking 21 or more cigarettes per day (FIG. 5).

The test substance containing theanine made the average smoking interval time period longer than that of the placebo, and thus a smoking suppressive effect was found as compared to the placebo. In addition, the test substance group statistically showed a significant difference against the placebo group in both of the two groups. Here, the test was carried out by Student paired t-test.

(iv) Continuous Intake Test Within A Day

1) Subject

As a subject, one subject (body weight: 74 kg) which was judged to be high level of dependency according to the above-mentioned nicotine dependency test was selected from the same participants as those in item (ii) Test 2 Immediately After Waking above. The subject was a male of age of 36, having a smoking career of 17 years.

2) Test

As theanine and a test substance, the same ones as those in item (ii) Test 2 Immediately After Waking above were used. The test was carried out within a day, which was repeated three time, i.e. the test was carried out on three separate days. The subject was allowed to take a test substance ad libitum whenever the subject craved for smoking during the period of waking to 8 o'clock in the evening. Also, the subject was allowed to freely smoke during this period. The subject was asked to record all the smoking time and the intake time of the test substance within a day in the questionnaire chart.

3) Results

Figure 6:
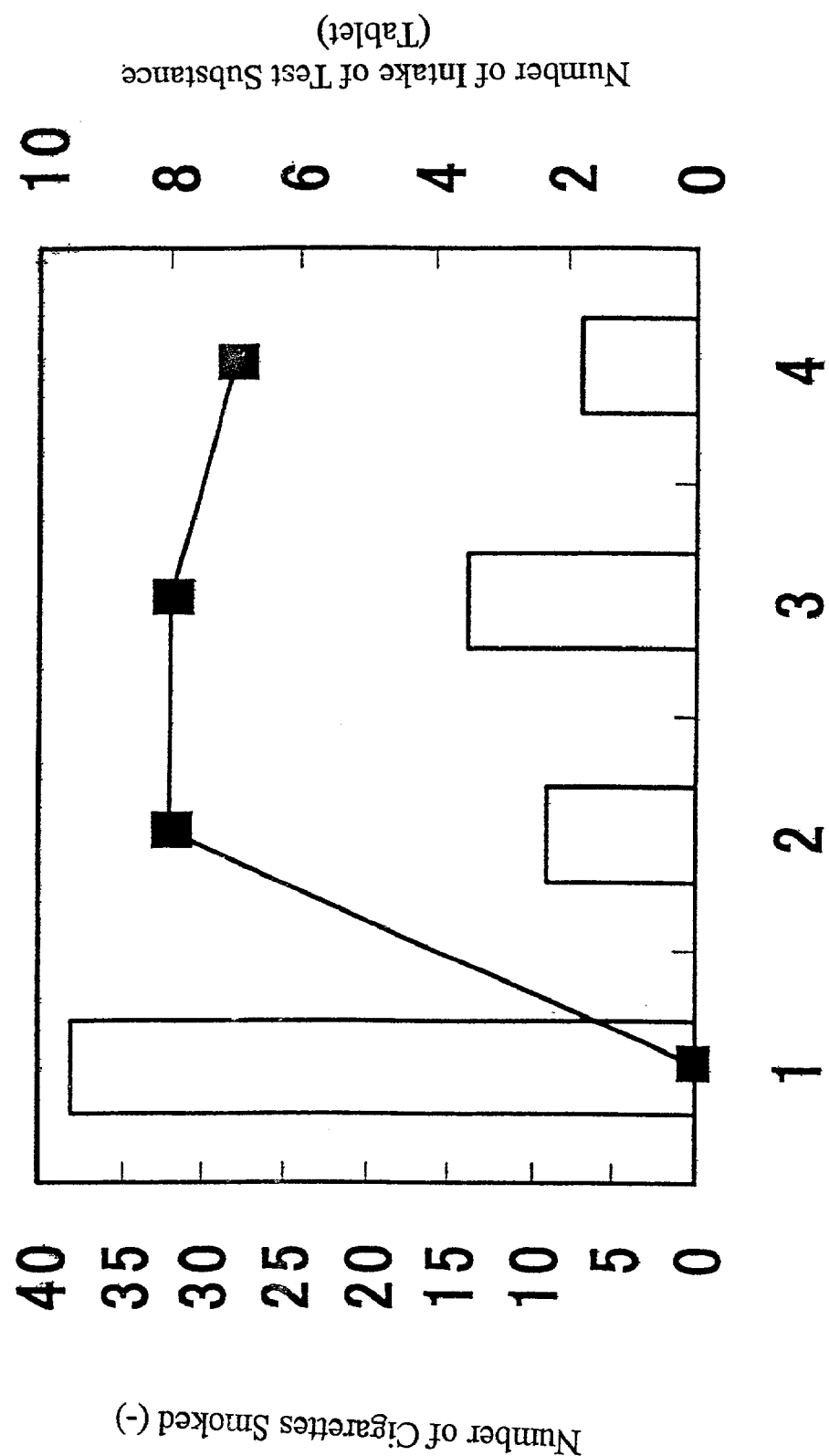
FIG. 6 shows a result of continuous intake test within a day, wherein a bar in the graph is the number of cigarettes smoked (-), and a solid square is the number of intake of the test substance (tablet), and numerical FIG. 1 in abscissa axis of the graph is the results of an any day without taking the test substance, and numerical

FIG. 6 is a graph showing the relationship between the number of cigarettes smoked in a case where the test substance was taken when the subject craved for smoking during the period of waking to 8 o'clock in the evening, and the number of intake of the test substance, the subject having a daily number of cigarettes puffed of nearly 40. While the number of daily intake of the test substance was of the level of 7 to 8 tablets, the number of cigarettes smoked was clearly reduced. Also, there was found especially no adverse effects.

(3) Long-Term Nicotine Dependency Calming Test

A suppressive effect for smoking by an intake of theanine for duration of a long term was studied by (i) a one-week continuous intake, and (ii) a one-month continuous intake.

(i) One-Week Continuous Intake Test

1) Subject

As a subject, one subject (body weight: 75 kg) which was judged to be high level of dependency according to the above-mentioned nicotine dependency test was selected from the same participants as those in item (ii) Test 2 Immediately After Waking above. The subject was a male of age of 51, having a smoking career of 33 years.

2) Test

As theanine and a test substance, the same ones as those in item (ii) Test 2 Immediately After Waking above were used. The test was carried out for one week. The subject was allowed to take a test substance ad libitum whenever the subject craved for smoking. Also, the subject was allowed to freely smoke during this period. The subject was asked to record all the smoking time and the intake time of the test substance during one week in the questionnaire chart.

3) Results

Figure 7:
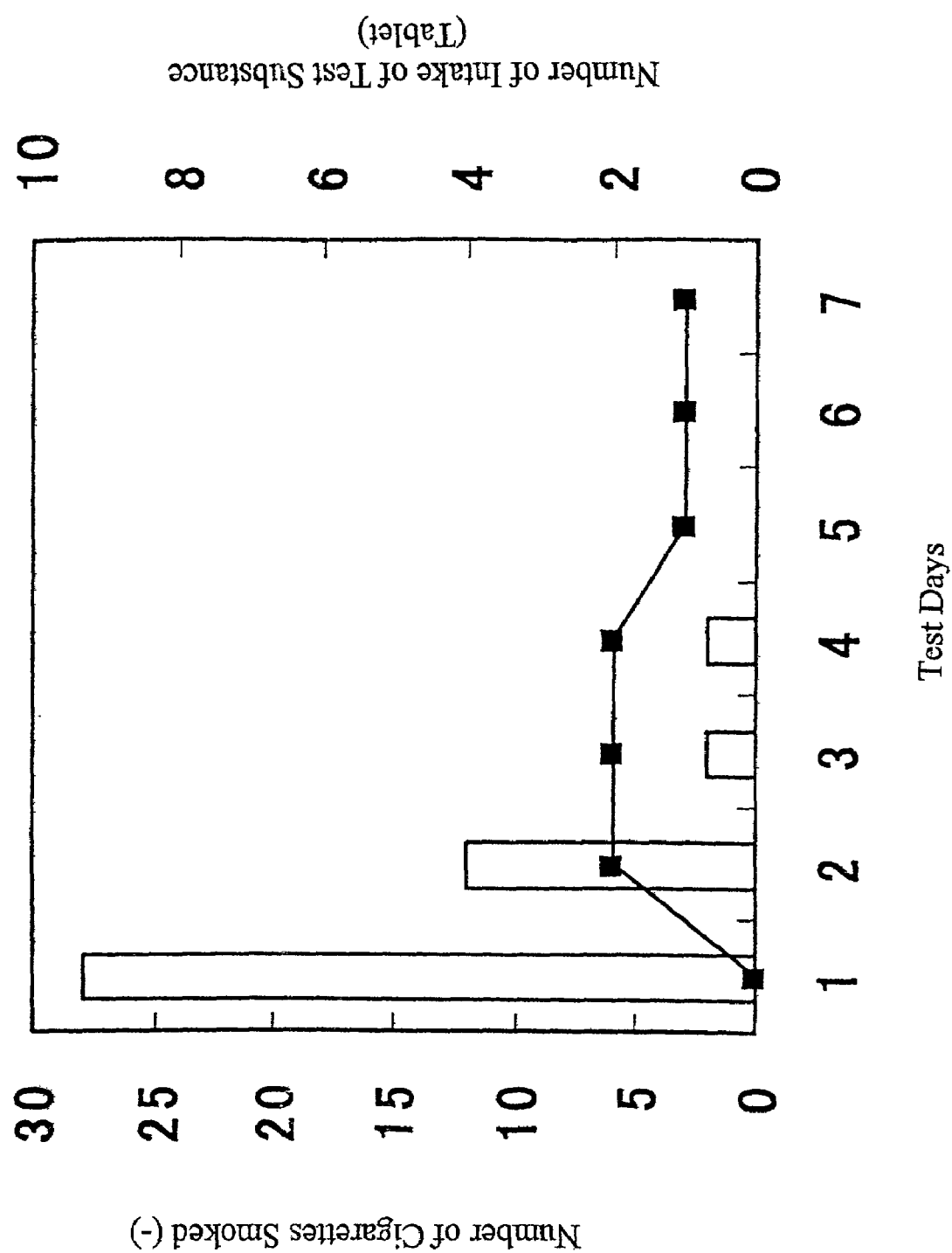
FIG. 7 shows the results of continuous intake test for one week, wherein a bar in the graph is the number of cigarettes smoked (-), and a solid square is the number of intake of the test substance (tablet).

FIG. 7 is a graph showing the relationship between the number of cigarettes smoked on a daily basis and the number of intake of the test substance. While the number of daily intake of the test substance was of the level of about 2 tablets, the subject, who was aiming to quit smoking taking the opportunity of this test, quitted smoking with the intake of one tablet of the test substance on day 5 and afterwards, whereby consequently succeeding in quitting smoking after one week from the initiation of the intake. Thereafter, the nonsmoking state continued even after a half year even without taking almost no theanine. Here, on day 1, the test substance was not taken.

(ii) One-Month Continuous Intake Test

An effect of the L-theanine formulated chewable tablet obtained in Example 2 was evaluated by a one-month continuous intake test conducted for 30 subjects (average body weight: 70 kg) who were judged to be the moderate level or higher in the selection of the subjects under item (1) above. As comparison, the control chewable tablet of Comparative Example 1 was subjected to the test.

The test was carried out in two divided groups of 15 subjects each. The subjects in each group were subjected to one-month continuous intake by taking the L-theanine formulated chewable tablet of Example 2 (Smoker Nos. 1 to 15) or the control chewable tablet of Comparative Example 1 (Smoker Nos. 16 to 30) in the amount of 2 tablets per day, one tablet each in the morning and in the afternoon with an interval of at least 5 hours. During the test period, each of the subjects was not informed which of the test substances was taken. Also, there were no especial restriction on their life including smoking except for the intake of the above-mentioned test substance within one day.

The changes in the average number of cigarettes smoked of each subject before and after the test were examined by the questionnaire survey, and the effects of the test substances were judged in accordance with the following evaluation criteria. The results are shown in Table 4.

| Evaluation Criteria | |
|---|---|
| ⊙ nonsmoking effect | (number of cigarettes smoked: 0) |
| ○ suppressive effect for craving for smoking | (number of cigarettes smoked: reduced by 10 or more) |
| Δ slight suppressive effect for craving for smoking | (number of cigarettes smoked: reduced by 5 to 9) |
| x no effect | (number of cigarettes smoked: other than the above) |

TABLE 4

| Smoker No. | No. of Cigarettes Before Test (/day) | No. of Cigarettes at Termination of Test (/day) | Evaluation of Effect |
|---|---|---|---|
| L-Theanine Chewable Tablet of Ex. 2 | | | |
| 1 | 40 | 30 | ○ |
| 2 | 40 | 25 | ○ |
| 3 | 35 | 0 | ⊙ |
| 4 | 45 | 40 | Δ |
| 5 | 30 | 15 | ○ |
| 6 | 25 | 0 | ⊙ |
| 7 | 45 | 20 | ○ |
| 8 | 55 | 50 | Δ |
| 9 | 45 | 40 | Δ |
| 10 | 35 | 5 | ○ |
| 11 | 40 | 35 | Δ |
| 12 | 45 | 10 | ○ |
| 13 | 35 | 0 | ⊙ |
| 14 | 60 | 45 | ○ |
| 15 | 50 | 45 | Δ |
| Control Chewable Tablet of Comp. Ex. 1 | | | |
| 16 | 45 | 35 | ○ |
| 17 | 35 | 35 | x |
| 18 | 40 | 40 | x |
| 19 | 45 | 45 | x |
| 20 | 60 | 55 | Δ |
| 21 | 50 | 45 | Δ |
| 22 | 50 | 50 | x |
| 23 | 35 | 30 | Δ |
| 24 | 40 | 40 | X |
| 25 | 40 | 40 | x |
| 26 | 40 | 45 | x |
| 27 | 55 | 45 | ○ |
| 28 | 30 | 30 | x |
| 29 | 45 | 40 | Δ |
| 30 | 45 | 45 | x |

According to the results shown in Table 4, the L-theanine formulated chewable tablet of Example 2 was found to have a nonsmoking effect or a suppressive effect for craving for smoking in all cases. On the other hand, the control chewable tablet prepared in Comparative Example 1 was found to have almost no such effects. Here, subjects No. 3, No. 6, No. 13, No. 16 and No. 27 were those who aimed to quit smoking taking the opportunity of this test. The subjects No. 16 and No. 27 using the control chewable tablet prepared in Comparative Example 1 could not attain nonsmoking, though the number of cigarettes smoked was slightly reduced.

Incidentally, during the test period, undesirable adverse action was not found at all, and further no dependency on the test substance was confirmed.

Test Example 2

A test was carried out on the changes in the blood theanine concentration when the L-theanine formulated chewable tablet was subjected to oral mucosa absorption or intestinal absorption. The subject was prohibited from taking any foodstuff other than water and smoking after waking.

(1) Oral Mucosa Absorption Test (i) Intake of Theanine: 87 mg

1) Subject

Among the same participants as those in item (ii) Test 2 Immediately After Waking above, a smoker showing high nicotine dependency [subject A (body weight: 78 kg)] was subjected to a test.

2) Test

As theanine and a test substance, the same ones as those in item (ii) Test 2 Immediately After Waking above were used. However, the test substance was taken in its half amount (theanine content: 87 mg).

The subject A was allowed to take the test substance by tasting the substance in the mouth after 150 minutes from waking. In addition, the subject was prohibited from smoking for 150 minutes after waking. Blood was collected before the intake of the test substance, and after 5 minutes, 10 minutes, 20 minutes, 30 minutes, 60 minutes, 90 minutes and 180 minutes from the intake. During the test, the subjects were asked to report their extent of craving for smoking according to the criteria shown in Table 5.

TABLE 5

| Evaluation Criteria | 0 | 1 | 2 | 3 | 4 |
|---|---|---|---|---|---|
| Extent | No craving for smoking | Slight craving for smoking | Mild craving for smoking | Moderate craving for smoking | High level of craving for smoking |

Here, the blood theanine concentration was determined by the following method.

Determination of Blood Theanine Concentration (a) Pretreatment of Blood

Each of the collected blood was distributed into a blood sampling tube (Venoject II Autosep, TERUMO CORPORATION), and centrifuged (3000 rpm for 10 minutes, himac CT 6D: Hitachi Koki Co., Ltd.) to collect sera. To 0.5 ml of each of the resulting sera was added 1.0 ml of acetonitrile, and the mixture was centrifuged (12000 rpm for 10 minutes, MR-150: K.K. Tommy Seiki) to collect the supernatant. The resulting supernatant was dried up with a centrifugal evaporator (Model "CVE-100D," Tokyo Rika Kikai K.K.), and 0.5 ml of distilled water was added to the resulting substance for dissolving it.

(b) Analysis of Theanine

The blood theanine concentration was determined in accordance with AccQ·Tag Amino Acid Analysis Method of Waters Corporation. Ten microliters of blood previously treated by filtering with a membrane filter (DISMIC 13CP: ADVANTEC), 10 μl of 10 ppm norleucine, which is an internal standard reagent, 60 μl of AccQ·Fluor Borate Buffer (Waters Corporation) and 20 μl of AccQ·Fluor Reagent (Waters Corporation) were mixed together and then derivatizing reaction was performed. The sample was analyzed by AccQ·Tag amino acid analysis column (3.9 mm×150 mm: Waters Corporation), and detected with the fluorescence spectrophotometer at an excitation wavelength of 250 nm and an emission wavelength of 395 nm. The quantification was made with a calibration curve method.

(ii) Intake of Theanine: 200 mg

As the test chewable tablet, the L-theanine formulated chewable tablet of Example 1 containing 200 mg of L-theanine was used. A smoker showing high nicotine dependency [the same subject A as in item (i) Intake of Theanine: 87 mg above] was subjected to this test. The subject A was allowed to take one tablet of chewable tablet of Example 1 with tasting for 6 minutes after 150 minutes from waking. In addition, the subject was prohibited from smoking for 150 minutes after waking. Blood was collected before the intake of the chewable tablet of Example 1, and after 5 minutes, 10 minutes, 20 minutes, 30 minutes, 60 minutes, 90 minutes and 180 minutes from the intake. During the test, the presence or absence and extent of craving for smoking was questioned according to the criteria shown in Table 5, and the withdrawal symptoms were observed. Here, the blood theanine concentration was determined in the same manner as in the case of item (i) Intake of Theanine: 87 mg above.

(2) Test of Intestinal Absorption

In the test of intestinal absorption, a nonsmoker (subject B) was subjected to a test, and the subject B was asked to immediately chew down and swallow one tablet of the chewable tablet of Example 1 after 150 minutes from waking. Blood was collected before the intake of the chewable tablet of Example 1, and after 5 minutes, 10 minutes, 20 minutes, 30 minutes, 60 minutes, 90 minutes and 180 minutes from the intake. Here, the blood theanine concentration was determined in the same manner as in the case of item (i) Intake of Theanine: 87 mg above.

Figure 8:
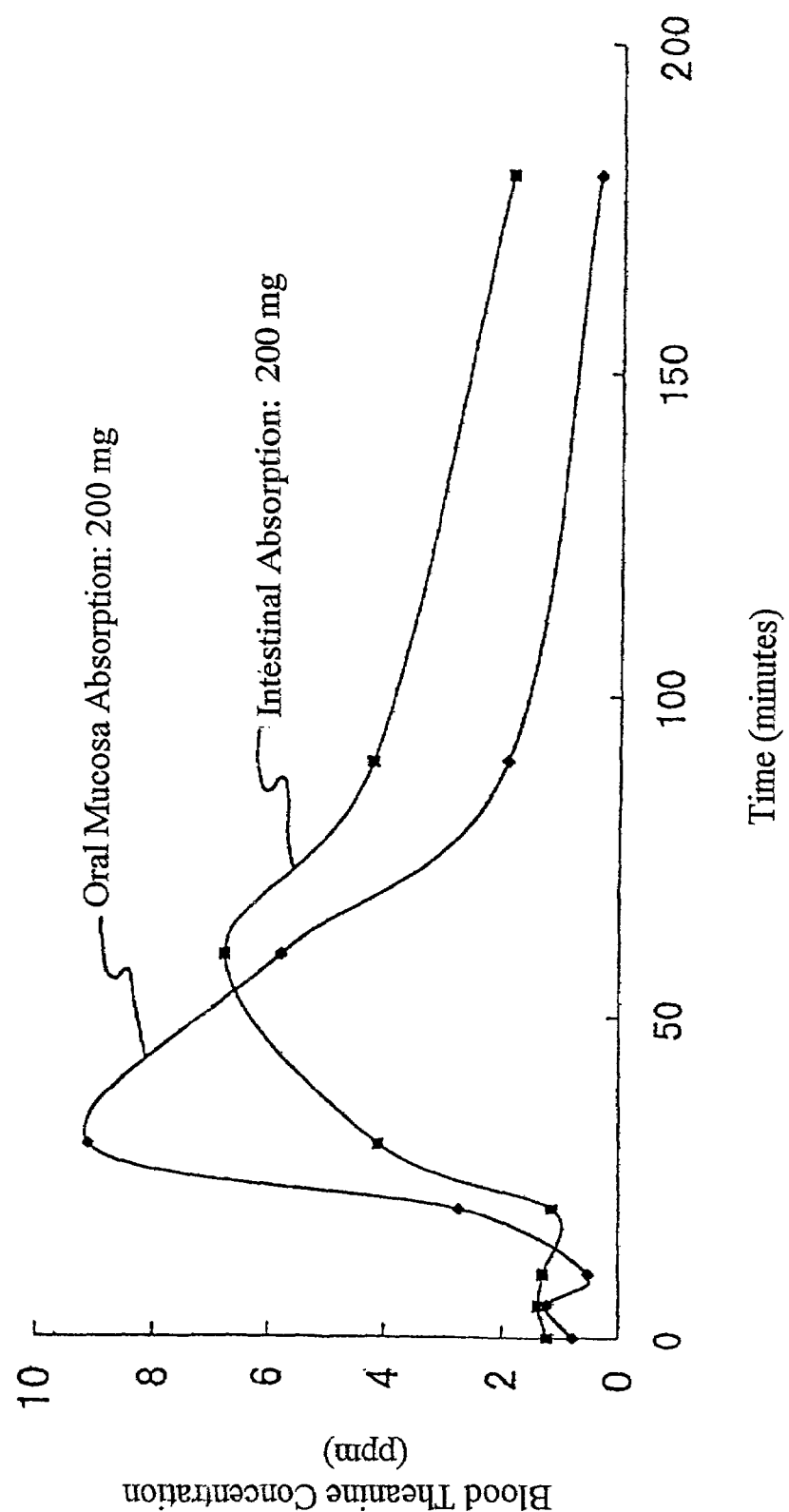
FIG. 8 shows changes in the blood theanine concentration in a case of oral mucosa absorption or intestinal absorption of an L-theanine formulated chewable tablet.

Test Results:

The changes in the blood theanine concentration (ppm) with the passage of time when the L-theanine formulated chewable tablet (theanine content: 200 mg) was subjected to oral mucosa absorption or intestinal absorption are shown in FIG. 8. As the oral mucosa absorption and the intestinal absorption are compared, the time period for reaching the maximal blood theanine concentration is shorter in the oral mucosa absorption, whereby confirming a quicker absorption in the oral mucosa absorption. In addition, from the fact that the maximal value of the blood theanine concentration is higher in the oral mucosa absorption, it was confirmed that the oral mucosa absorption shows a good absorption rate. However, the blood theanine concentration was sustained for a longer duration in the intestinal absorption.

In addition, in item (1) oral mucosa absorption test above, cravings for smoking before, during and after the test were monitored with the passage of time as mentioned above. The changes in the cravings for smoking with the passage of time and the changes in the blood theanine concentration when theanine was taken in an amount of 87 mg, and when theanine was taken in an amount of 200 mg are shown in FIGS. 9 and 10, respectively.

Figure 9:
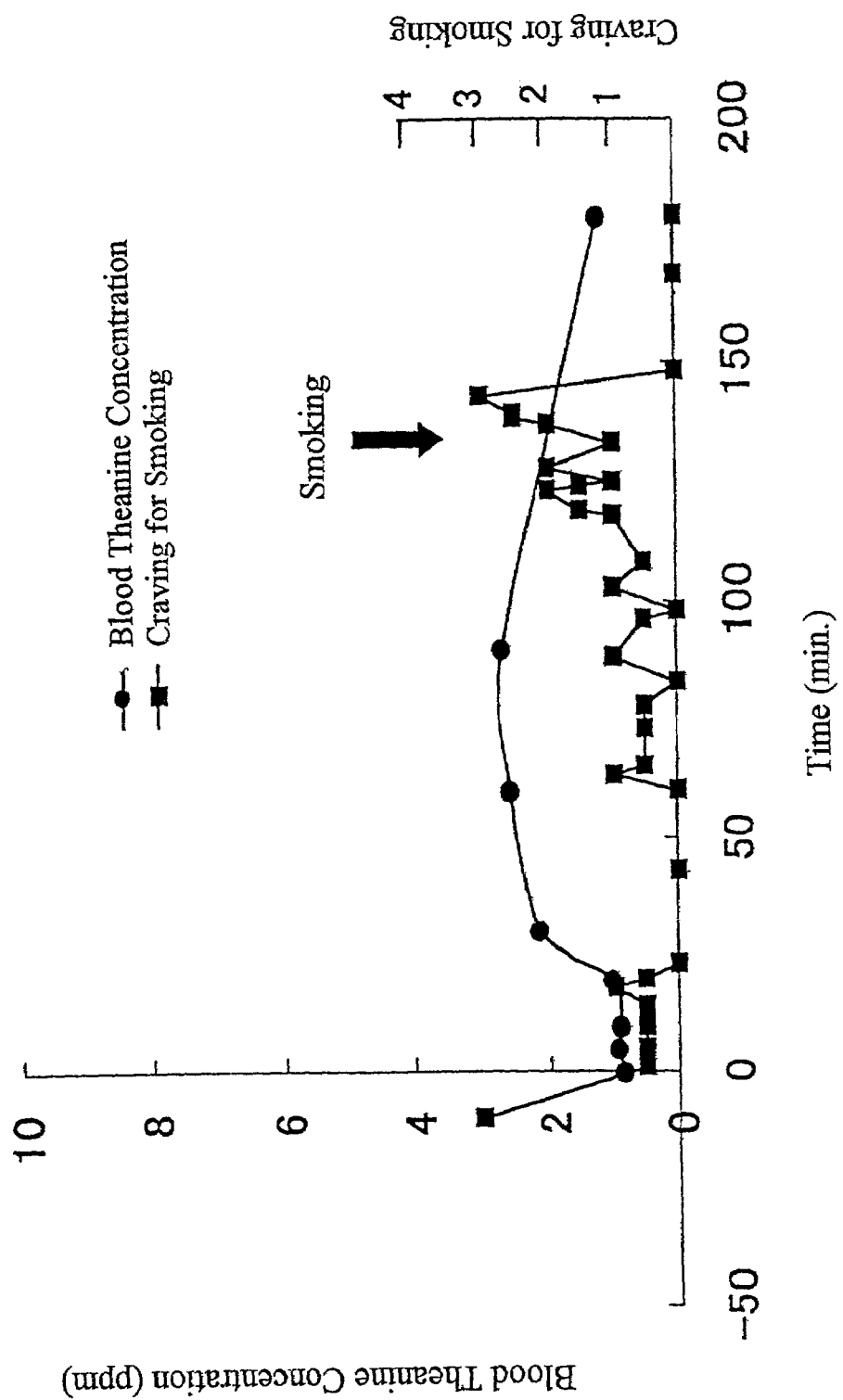
FIG. 9 shows changes in craving for smoking with the passage of time and the blood theanine concentration when a subject is allowed to take 87 mg of theanine.
Figure 10:
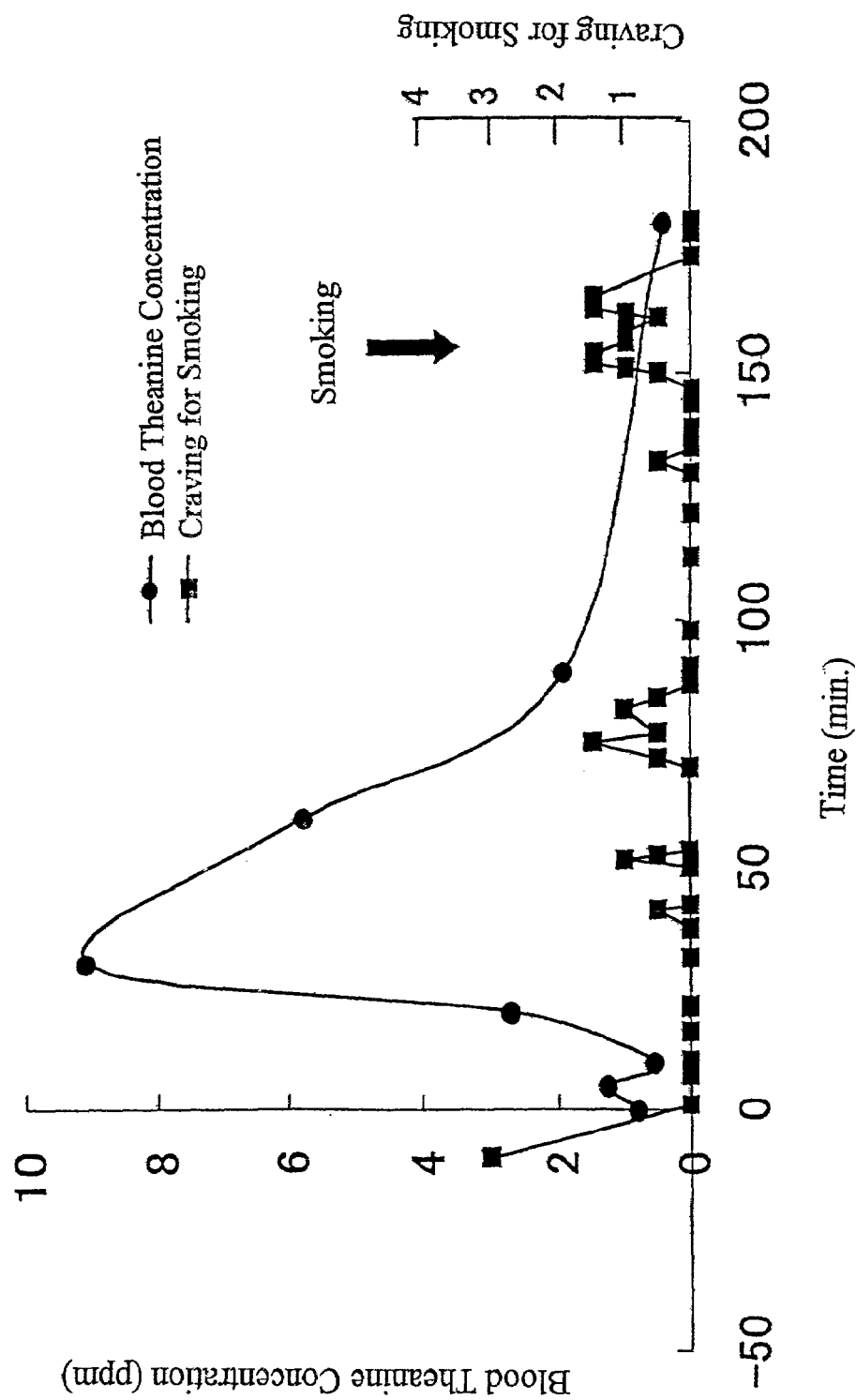
FIG. 10 shows changes in craving for smoking with the passage of time and the blood theanine concentration when a subject is allowed to take 200 mg of theanine.

As shown in FIG. 9, the cravings for smoking of the subject A before, during and after the test were monitored with the passage of time. Immediately before taking the test substance, since the subject was prohibited from smoking for 150 minutes after waking, there was occurrence of a strong craving for smoking, and moderate withdrawal symptoms were found. However, after the intake, the craving for smoking dramatically disappeared, and thereafter the changes in the craving for smoking were suppressed almost in a blood theanine concentration-dependent manner. As compared to the case of intake of theanine: 200 mg, the blood theanine concentration of the case of intake of theanine: 87 mg is low, so that the craving for smoking is relatively high from the beginning of the test, and the craving for smoking appears after 60 minutes, and the craving cannot be suppressed after 140 minutes and the subject smokes thereat. As a result, the subject did not smoke for 290 minutes after waking. On the other hand, as shown in FIG. 10, in the case of intake of theanine: 200 mg, the cravings for smoking of the subject A before, during and after the test were monitored with the passage of time. Immediately before taking the L-theanine formulated chewable tablet, since the subject was prohibited from smoking for 150 minutes after waking, there was occurrence of a strong craving for smoking, and moderate withdrawal symptoms were found. However, after the intake, the craving for smoking dramatically disappeared, and thereafter the changes in the craving for smoking, with some variations, were suppressed almost in a blood theanine concentration-dependent manner. The craving for smoking appeared at a point of 150 minutes after the beginning of the test, and the subject finally smoked at a point of 165 minutes. Consequently, the subject did not smoke for 315 minutes after waking. The subject A had a habit of usually smoking immediately after waking, but it is found that his craving for smoking can be effectively suppressed by taking theanine in an amount of about 90 to about 200 mg. In addition, the suppressive effect was deduced to be associated with the changes in the blood theanine concentration.

Summary of Test Examples 1 and 2

In the short-term nicotine dependency calming test, tests were conducted immediately after waking, at which the body nicotine concentration is presumably at the lowest level and in a daytime, at which the body nicotine concen tration is presumably at a high level. In either case, a significant suppressive effect for smoking was exhibited by an intake of theanine (200 mg) in subjects of which nicotine dependencies were judged moderate level or higher. Especially, "Daytime Test" was performed in an actual business location. Although there would be various factors (noise) inducing smoking, an effect of theanine could be confirmed. In addition, in the continuous intake within a day which was also performed, the effect of intake of theanine was tested in a usual life, wherein a significant decrease in the number of cigarettes smoked was seen.

In addition, in the long-term nicotine dependency calming test, even with a one-week continuous intake of theanine of about 400 mg per day, it was shown that the subject may result in quitting smoking in some cases. During a one-month continuous intake, a nonsmoking effect or a suppressive effect for craving for smoking was found in all the cases of the recipients. Also, no undesirable adverse action or theanine dependencies were found.

On the other hand, in the oral mucosa absorption test and the intestinal absorption test, it was shown that the theanine was more quickly absorbed via the oral mucosa and its absorption rate was higher, as compared to the intestinal absorption, and that the suppressive effect for craving for smoking by the theanine was associated with the blood theanine concentration.

It is seen from the above that according to the composition for suppressing craving for smoking comprising theanine of the present invention, the craving for smoking can be significantly suppressed by a suitable intake of the composition, even in a smoker whose nicotine dependency level is moderate or higher, whereby intentional (when unrestricted) prohibition or moderation of smoking, and complete elimination of the smoking habit can be safely and effectively achieved. In addition, it is seen that the intake of theanine is more effective by carrying out with a composition suitable for absorption via the oral mucosa as concretely illustrated herein.

INDUSTRIAL APPLICABILITY

According to the present invention, there is provided a composition for suppressing craving for smoking whichexhibits excellent effects such that there can be safely and effectively performed (1) suppression of craving for smoking in a situation where nonsmoking is mandatory in daily life; (2) intentional prohibition or moderation of smoking (when unrestricted); and (3) complete elimination of the smoking habit.

The invention claimed is:

1. A method for suppressing craving for smoking or moderating smoking, comprising
   administering to an individual a smoking craving suppressing composition consisting essentially of theanine in an amount sufficient to suppress craving for smoking wherein the composition is a preparation suitable for absorption via oral mucosa.

2. The method according to claim 1, wherein the composition is administered to an individual for alleviating withdrawal symptoms caused by stopping smoking or moderation of smoking.

3. The method according to claim 1, wherein the composition is previously administered to an individual when withdrawal symptoms are presumed to be caused by stopping smoking or moderation of smoking.

4. The method according to claim 1, wherein the composition is administered to an individual during occurrence of withdrawal symptoms caused by stopping smoking or moderation of smoking.

5. The method according to claim 1, wherein the composition is in a dosage form sustainable in the mouth for at least 3 minutes when orally taken.

6. The method according to claim 1, wherein the composition is a food composition.

7. The method according to claim 1, wherein the composition is administered to an individual in an amount of from 87 mg to 200 mg.

* * * * *